US012383654B1

(12) United States Patent
Zhu et al.

(10) Patent No.: US 12,383,654 B1
(45) Date of Patent: Aug. 12, 2025

(54) ACELLULAR MATRIX WOVEN MATERIAL, PREPARATION METHOD AND APPLICATION THEREOF

(71) Applicant: Nankai University, Tianjin (CN)

(72) Inventors: Meifeng Zhu, Tianjin (CN); Guangzhou Song, Tianjin (CN); Wenqian Cong, Tianjin (CN); Wen Li, Tianjin (CN); Kai Wang, Tianjin (CN); Deling Kong, Tianjin (CN)

(73) Assignee: Nankai University, Tianjin (CN)

( * ) Notice: Subject to any disclaimer, the term of this patent is extended or adjusted under 35 U.S.C. 154(b) by 0 days.

(21) Appl. No.: 19/014,573

(22) Filed: Jan. 9, 2025

(30) Foreign Application Priority Data

May 10, 2024 (CN) .......................... 202410576320.5

(51) Int. Cl.
*A61L 27/36* (2006.01)
*B33Y 10/00* (2015.01)
*D03D 15/20* (2021.01)
*D03D 25/00* (2006.01)

(52) U.S. Cl.
CPC ....... *A61L 27/3633* (2013.01); *A61L 27/3691* (2013.01); *B33Y 10/00* (2014.12); *D03D 15/20* (2021.01); *D03D 25/005* (2013.01)

(58) Field of Classification Search
None
See application file for complete search history.

(56) References Cited

U.S. PATENT DOCUMENTS

| | | | |
|---|---|---|---|
| 2005/0273155 A1 | 12/2005 | Bahler et al. | |
| 2016/0213815 A1 | 7/2016 | Watschke | |
| 2020/0330644 A1* | 10/2020 | MacQueen | ............ B33Y 70/00 |
| 2023/0405186 A1 | 12/2023 | Zhu | |

FOREIGN PATENT DOCUMENTS

| | | | |
|---|---|---|---|
| CN | 105531410 A | | 4/2016 |
| CN | 106215241 A | | 12/2016 |
| CN | 106693065 A | | 5/2017 |
| CN | 108310463 | * | 7/2018 |
| CN | 109453428 A | | 3/2019 |
| CN | 109996912 A | | 7/2019 |
| CN | 114984320 A | | 9/2022 |
| CN | 115382023 | * | 11/2022 |
| CN | 118512659 A | | 8/2024 |
| WO | 2015032426 A | | 3/2015 |
| WO | 2018097737 A | | 5/2018 |

OTHER PUBLICATIONS

Machine Translation of CN 106215241 (Year: 2016).*

(Continued)

*Primary Examiner* — Shawn McKinnon
(74) *Attorney, Agent, or Firm* — Pilloff Passino & Cosenza LLP; Rachel Pilloff; Sean Passino

(57) ABSTRACT

An acellular matrix woven material, a preparation method and an application thereof are provided. The acellular matrix woven material is prepared by combining 3D printing with weaving. At the same time, also provided are the acellular matrix woven material prepared by the preparation method and its application in preparing tissue engineering scaffold materials.

4 Claims, 16 Drawing Sheets

(56) References Cited

OTHER PUBLICATIONS

Machine Translation of CN115382023 (Year: 2022).*
Machine Translation of CN108310463 (Year: 2018).*
Retrieval report-First search dated Sep. 25, 2024 in SIPO application No. 202410576320.5.
Retrieval report-Supplementary search dated Oct. 31, 2024 in SIPO application No. 202410576320.5.
Notification to Grant Patent Right for Invention dated Nov. 7, 2024 in SIPO application No. 202410576320.5.
Ju Zhang et al., dECM restores macrophage immune homeostasis and alleviates iron overload to promote DTPI healing, Regenerative Biomaterials, Jan. 17, 2024, vol. 11, rbad118, pp. 1-14 doi: 10.1093/rb/rbad118 Full text; Claims involved: 1-6.
Laure Magnan, et al., Human textiles: A cell-synthesized yarn as a truly "bio" material for tissue engineering applications, Acta Biomaterialia, Jan. 26, 2020, vol. 105, pp. 111-120 doi: 10.1016/j.actbio.2020.01.037 Full text; Claims involved: 1-6.
Notice of first Office action dated Sep. 30, 2024 in SIPO application No. 202410576320.5.

\* cited by examiner

Hematoxylin eosin staining  Nuclear staining

ACELLULAR MATRIX WOVEN MATERIAL, PREPARATION METHOD AND APPLICATION THEREOF

CROSS-REFERENCE TO RELATED APPLICATIONS

This application claims priority to Chinese Patent Application No. 202410576320.5, filed on May 10, 2024, the contents of which are hereby incorporated by reference.

TECHNICAL FIELD

The disclosure belongs to the technical field of biomaterials, in particular to an acellular matrix woven material, a preparation method and an application thereof.

BACKGROUND

Fiber fabric scaffold materials have a wide range of application scenarios in tissue repair, and are used to repair tissue wounds such as bone, cartilage, heart, blood vessels, nerves, achilles tendon, tendon, ligament, muscle and skin. Conventional biomedical textile materials are mainly synthetic polymers and natural materials. Synthetic materials such as polyester, polypropylene, polytetrafluoroethylene, polycaprolactone and polylactic acid have high mechanical strength and are easy to process, but they lack biological activity and have limited ability to promote tissue repair. Natural materials such as collagen, gelatin, silk fibroin and chitosan have good biocompatibility, but their mechanical properties and processability are poor. Acellular matrix materials are obtained by decellularization of tissues by physical, chemical or biological ways. The acellular matrix material has good biocompatibility. The acellular matrix materials are biocompatible and rich in active factors capable of modulating the immune microenvironment, and are used for cell loading and in vitro tissue engineering, as well as in vivo implantation to promote physiological tissue remodeling. However, the acellular matrix material obtained by direct decellularization of tissues has a compact structure, and cells are difficult to penetrate into the material, resulting in poor cell migration and limiting its application in cell loading and tissue regeneration. Acellular matrix hydrogels are used for cell loading, but their mechanical properties are weak, limiting the effectiveness of cell therapy. Bi Weiwei et al. load cells onto acellular amniotic membrane sheets, but the cell loading rate is low due to the lack of pore structure. Effective strategies and processes to construct acellular matrix scaffold materials for cell loading and tissue repair are still lacking.

In the prior art, Nicolas L 'heureux laboratory in France has successively established two processes to prepare acellular matrix fibers for weaving artificial blood vessels. In 2020, firstly, fibroblasts are prepared by in vitro culture, and then decellularization was carried out, and further cut into acellular matrix fibers for weaving artificial blood vessels. However, cell culture is harsh and expensive, so it is difficult to realize large-scale production. Then in 2022, he adopted a new acellular matrix raw material, cut the human fetal membrane into fibers after decellularization and further twisted it into threads for weaving artificial blood vessels, thus avoiding the defects of the above process. However, the sizes of amniotic membrane are limited, so it is difficult to cut off acellular matrix fibers long enough to produce artificial blood vessels matching the size of human body. Wang Guifa cut the cattle casing into pieces with uniform width with a cutter, degreased, washed and twisted, and then used to make suture. The length of cattle casing is limited, so it is not enough to produce large-size scaffold materials for repairing large-volume tissue defects of human body. Up to now, there is still a lack of effective strategies and processes to produce long acellular matrix fibers for weaving scaffold materials that match human tissues, loading cells and promoting tissue repair.

In terms of structural design and construction of scaffold materials, 3D scaffold materials with certain dimensions may also be manufactured by certain textile techniques in the prior art, for example, the ways disclosed in CN109996912 A and CN 105531410 A. However, these conventional weaving ways have complicated processes and are difficult to accurately control the micro and macro structural shapes of fibers at the same time.

Therefore, it is an urgent technical problem for technicians in this field to realize the fine control of the material structure of acellular matrix scaffold, so as to improve the effect of cell loading and tissue repair.

SUMMARY

In order to solve the above technical problems, the disclosure provides an acellular matrix woven material, and a preparation method and an application thereof.

In order to achieve the above purpose, the present disclosure provides following technical schemes.

a preparation method of the acellular matrix woven material is provided, and the acellular matrix woven material is prepared by 3D printing in conjunction with the weaving method.

Optionally, the method specifically includes following steps:

The acellular animal tubular tissue is cut and twisted by a rotary cutting method, and then the weft part is printed in 3D and then the warp part is woven to obtain the acellular matrix woven material.

The disclosure has the advantages that the activity of acellular matrix fibers is fully maintained, and the advantages of 3D printing and textile technology in fine control of macro and micro structures of materials may be combined.

Optionally, the animal tubular tissue is one among small intestine, large intestine, artery and vein;

The animals include one or more among pigs, cattle, sheep, dogs, horses, rats and rabbits.

Beneficial effects: the acellular matrix fiber in the disclosure is obtained by rotary cutting, the effective use length is increased, suitable for various tubular tissue of various animals, and the source of raw materials is relatively wide.

Optionally, the decellularization includes the following steps:

The animal tubular tissue is put into peracetic acid solution, stirred and disinfected, then washed with water, then washed with sodium dodecyl sulfate solution. Then, first water washing and enzyme washing with Tris-HCL solution containing DNA and RNA enzymes in turn are carried out. After the second washing, the acellular process is completed, and the decellularized animal tubular tissue is obtained.

Beneficial effects: different from the conventional catgut decellularization with alkaline solution, the sodium dodecyl sulfate complex enzyme used in the disclosure has better decellularization and immunogenicity removal effects.

Optionally, the mass concentration of the peracetic acid solution is 0.1%;

The mass concentration of the sodium dodecyl sulfate solution is 1%;

The Tris-HCL solution containing DNA and RNA enzymes includes 50 units/mL of DNA enzymes and 1 unit/mL of RNA enzymes.

Beneficial effects: in the above process, 0.1% peracetic acid is enough for sterilization, and 1% sodium dodecyl sulfate achieve the effect of decellularization and immunogenicity removal, without leaving much residue.

Optionally, the stirring rate of the stirring disinfection is 60 r/min and the time is 2 hours (h).

The stirring rate of washing with sodium dodecyl sulfate solution is 50 r/min, and the washing time is 1 day, where the sodium dodecyl sulfate solution is changed every 8 h.

The stirring rate of the first water washing is 80 r/min, and the washing time is 3 days, in which the washing water is changed every 3 h.

The stirring speed of the enzyme washing is 70 r/min, the temperature is 37° C. and the time is 10 h.

The time of the secondary water washing is 3 days.

Beneficial effects: the above-mentioned high-frequency washing with changing water effectively removes residual reagents.

Optionally, the rotary cutting method includes following steps:

the acellular animal tubular tissue is sleeved on a cylindrical mold and fixed on a rotary cutting device, and then cut with a knife or laser in a spiral trajectory to obtain a continuous acellular matrix strip.

Beneficial effects: compared with the conventional longitudinal direct cutting, the rotary cutting method in the disclosure obtains acellular matrix fibers several times its own length, and the usable effective length is larger.

Optionally, the twisting is to twist the acellular matrix strip into fiber by using twisting equipment and wind it on a bobbin.

Beneficial effect: after rotary cutting, acellular matrix strips are obtained, and after twisting, the strips are curled into fibers.

Optionally, the 3D printing of the weft part and the weaving of the warp part specifically include following steps:

According to the required macro-shape, the weaving structure of the scaffold material is designed, and the corresponding G code is written. The acellular matrix fibers are printed on the platform with regularly arranged needle tubes, and the weft of the scaffold material is woven, and the needle tubes are replaced by acellular matrix fibers to weave the warp of the scaffold material.

Beneficial effect: the disclosure has the advantages that the conventional weaving process is complicated, and the three-dimensional weaving is difficult. By combining 3D printing and weaving, the macro and micro structures of the three-dimensional fabric may be finely constructed.

An acellular matrix woven material is obtained by a method of preparing an acellular matrix woven material.

Optionally, the micro-woven structure of the acellular matrix woven material is one among plain weave, twill weave and satin weave fixed by interweaving and interlocking warp and weft.

Beneficial effects: the fabric prepared by combining 3D printing and knitting in the disclosure belongs to warp and weft interweaving in structure, and can weave plain weave, twill weave and satin weave which are common fabrics.

The acellular matrix fiber woven material is applied in preparing the tissue engineering scaffold material.

Optionally, the acellular matrix fiber woven material is directly used for in vivo transplantation; and alternatively, cells are loaded on the acellular matrix fiber weaving in a direct planting mode, a flow culture mode or a hydrogel coating manner after transplantation application.

Optionally, the cell is one among smooth muscle cells, neuronal cells, endocrine cells, leukocytes, erythrocytes, phagocytes, epithelial cells, or stem cells.

Beneficial effects: the acellular matrix used in the disclosure has good biological activity and is beneficial to cell adhesion and proliferation; fabric structure has many pores, which may improve cell loading efficiency and will not block metabolism and nutrient diffusion.

Compared with the prior art, the disclosure has following advantages and technical effects:

Long acellular matrix fibers are prepared by the preparation method provided by the disclosure, and the fine control of macro-structure and micro-structure of acellular matrix fiber woven materials is realized by using 3D printing technology to assist weaving. Compared with the conventional acellular matrix scaffold materials, the acellular matrix fiber scaffold prepared by 3D printing significantly improves cell loading efficiency, accelerates rapid cell migration, and promotes endogenous tissue regeneration. In addition, scaffold materials with different shapes are prepared by using the method in the disclosure, and are used for repairing various tissues such as muscles and blood vessels. In addition, the acellular matrix fiber provided by the disclosure is accelerated in degradation speed, releases various active factors to accelerate tissue repair, provides a real acellular matrix microenvironment, improves cell loading efficiency and survival, and promotes cell migration, proliferation and differentiation, and is an excellent cell transplantation carrier.

BRIEF DESCRIPTION OF THE DRAWINGS

The accompanying figures, which constitute a part of this disclosure, are used to provide a further understanding of the disclosure. The illustrative embodiments of this disclosure and their descriptions are used to explain this disclosure, and do not constitute an improper limitation of this disclosure. In the figures.

DETAILED DESCRIPTION OF THE EMBODIMENTS

Figure 1A:
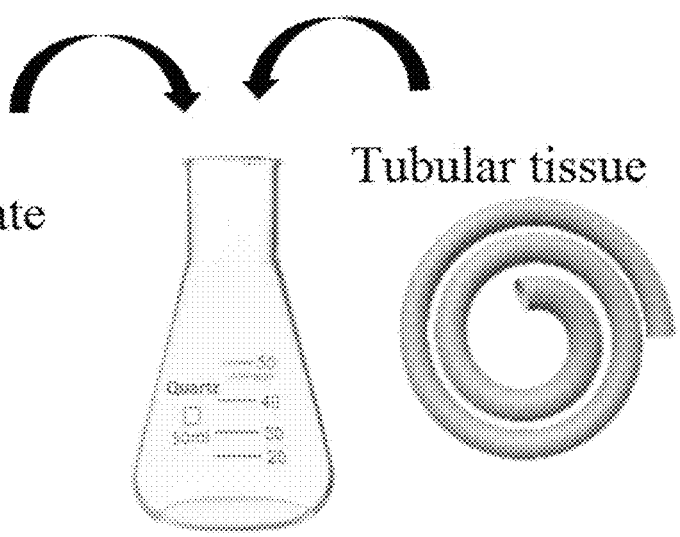
FIG. 1A is the schematic diagram of decellularization of animal tubular tissue.

In the following, the technical schemes in the embodiments of the disclosure will be clearly and completely described with reference to the figures. Obviously, the described embodiments are only a part of the embodiments of the disclosure, but not all embodiments. Based on the embodiments in the present disclosure, all other embodiments obtained by a person of ordinary skill in the art without making creative labor fall within the scope of protection of the present disclosure.

In order to make the above objects, features and advantages of the present disclosure more obvious and easier to understand, the present disclosure will be further described in detail with the figures and specific embodiments.

The embodiment of the disclosure provides a method for preparing an acellular matrix woven material, and the acellular matrix woven material is prepared by combining 3D printing with weaving.

An optional embodiment specifically includes following steps:
the decellularized animal tubular tissue is cut and twisted by a rotary cutting method, and then the weft part is printed in 3D and then the warp part is woven to obtain the acellular matrix woven material.

In an optional embodiment, the animal tubular tissue is one among small intestine, large intestine, artery and vein; The animals include one or more among pigs, cattle, sheep, dogs, horses, rats and rabbits.

In an optional embodiment, the decellularization includes following steps:
the animal tubular tissue is put into peracetic acid solution, stirred and disinfected, and then washed with water, and then washed with sodium dodecyl sulfate solution. Then, first water washing and enzyme washing with Tris-HCL solution containing DNA and RNA enzymes in turn are carried out. After the second washing, the acellular process is completed, and the decellularized animal tubular tissue is obtained.

In an optional embodiment, the mass concentration of the peracetic acid solution is 0.1%;
the mass concentration of the sodium dodecyl sulfate solution is 1%;
the Tris-HCL solution containing DNA and RNA enzymes includes 50 units/mL of DNA enzymes and 1 unit/mL of RNA enzymes.

In an optional embodiment, the stirring rate of the stirring disinfection is 60 r/min and the time is 2 hours (h).

The stirring rate of washing with sodium dodecyl sulfate solution is 50 r/min, and the washing time is 1 day, where the sodium dodecyl sulfate solution is changed every 8 h.

The stirring rate of the first water washing is 80 r/min, and the washing time is 3 days, in which the washing water is changed every 3 h.

The stirring speed of the enzyme washing is 70 r/min, the temperature is 37° C. and the time is 10 h.

The time of the second water washing is 3 days.

In an optional embodiment, the rotary cutting method includes the following steps:
The acellular animal tubular tissue is sleeved on a cylindrical mold, fixed on a rotary cutting device, and then cut with a knife or laser in a spiral trajectory to obtain a continuous acellular matrix strip.

In an optional embodiment, the twisting is to twist the acellular matrix strip into fiber by using twisting equipment and wind it on a bobbin.

In an optional embodiment, the 3D printing of the weft part and the weaving of the warp part specifically include following steps:
according to the required macro-shape, the weaving structure of the scaffold material is designed, and the corresponding G code is written. The acellular matrix fiber is printed on the platform with regularly arranged needle tubes, and the weft part of the scaffold material is woven, and the needle tubes are replaced by acellular matrix fibers to weave the warp of the scaffold material.

The embodiment of the disclosure also provides a method for preparing the acellular matrix woven material.

In an optional embodiment, the micro-woven structure of the acellular matrix woven material is one among plain weave, twill weave and satin weave fixed by interweaving and interlocking warp and weft.

The embodiment of the disclosure also provides an application of the acellular matrix fiber woven material in preparing tissue engineering scaffold materials.

In an optional embodiment, the acellular matrix fiber woven material is directly applied for transplantation; and alternatively,
cells are loaded on the acellular matrix fiber woven material by direct planting, flow culture or hydrogel coating, and then transplanted for application.

In an optional embodiment, the cell is one among smooth muscle cells, neuronal cells, endocrine cells, leukocytes, erythrocytes, phagocytes, epithelial cells, or stem cells.

The raw materials in the embodiments of the present disclosure are all commercially available.

Unless otherwise specified, the room temperature mentioned in the embodiments of the disclosure refers to 25±2° C.

The animal tubular tissue in the embodiments of the disclosure are all purchased from slaughterhouses (Tianjin Ershang Yingbin Meat Food Co., Ltd.).

In the following embodiments, the operation flow of 3D printing only needs to follow the requirements of the equipment specification, and the G code design of structural design is also in accordance with the structural requirements of the final product, which belong to the conventional operation flow and are well known to those skilled in the art.

Embodiment 1

Figure 1B:
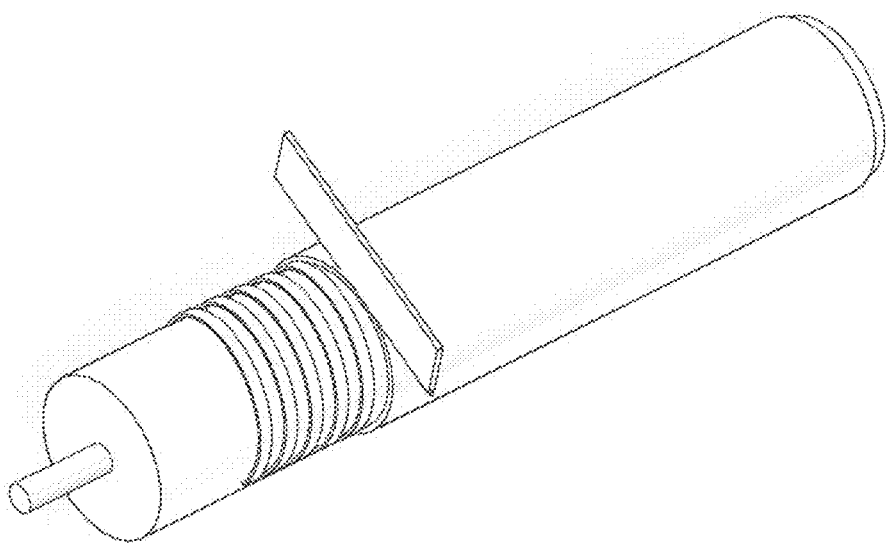
FIG. 1B is the rotary cutting mode diagram of tubular tissue.
Figure 1C:
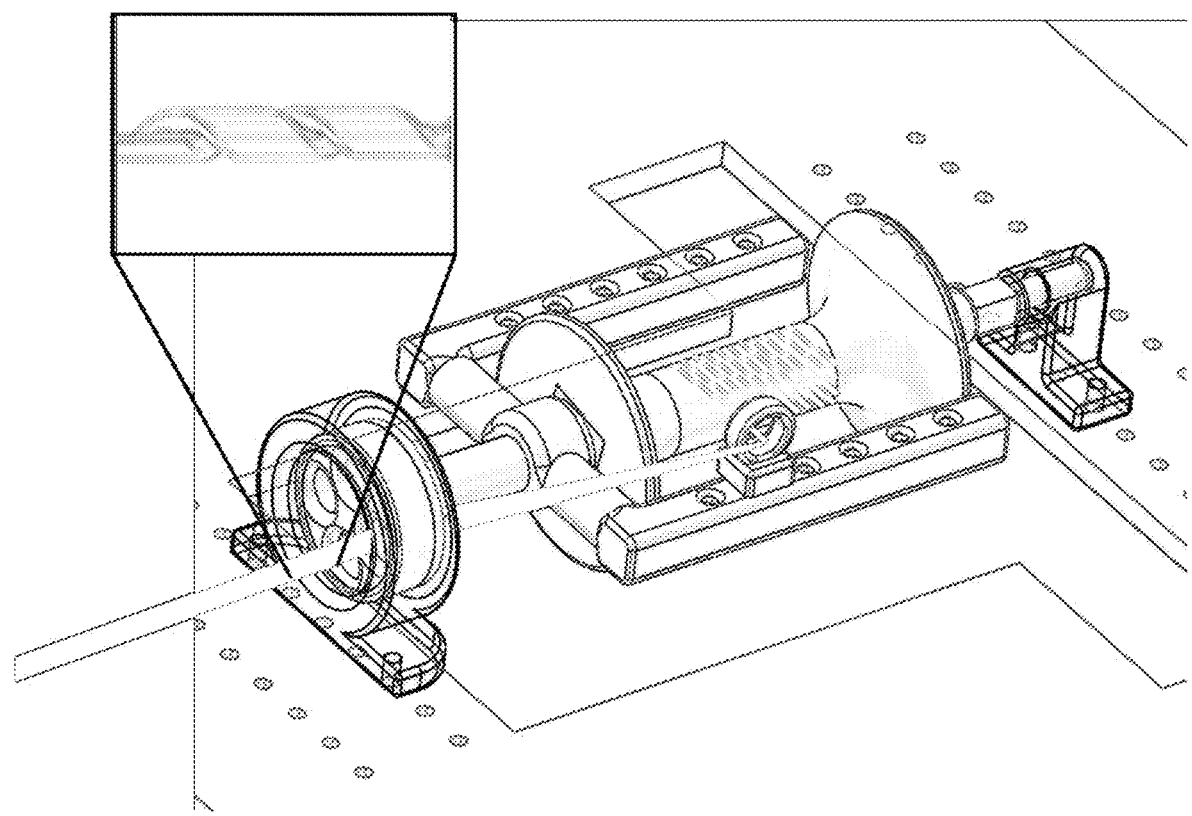
FIG. 1C is the twisting mode diagram of tubular tissue strip.

A preparation method of spongy porcine small intestinal submucosa acellular matrix fiber scaffold includes following steps:
S1, decellularization: the whole or part of porcine small intestinal submucosa is put into 0.1% peracetic acid solution according to the mass ratio of tissue to solution of 1:5, and stirred for 2 h at the rate of 60 r/min for disinfection. Take it out, wash it with water for three times, put it into 1% sodium dodecyl sulfate solution according to the mass ratio of tissue to solution of 1:5, stir and wash at 50 r/min, change the solution every 8 hours and wash for 1 day. Then, according to the mass ratio of tissue to water of 1:5, water is stirred and washed at the stirring speed of 80 r/min, and the solution is changed every 3 h, and washed for 3 days respectively. Tissue and solution are washed with Tris-HCL solution (50 units/mL DNA enzymes+1 unit/mL RNA enzymes) containing DNA and RNA enzymes according to the mass ratio of 1:5 at 70 r/min and 37° C. enzyme washing for 10 h, then taken out and washed with water for 3 days to obtain acellular tubular tissue (in FIG. 1A and FIG. 1E). As can be seen from the FIG. 1E, the nucleus is completely removed by H&E staining, and a large amount of acellular matrix remains.

S2, rotary cutting: the acellular tubular tissue is sleeved on a metal rod, and then the metal rod is fixed on a rotary cutting device, and the surface of the rod is rotary cut by using a cutter in a spiral trajectory (in FIG. 1B), and the rotation speed of the metal rod is set at 50 r/min, and the transverse speed of the cutter is 30 mm/min, 20 mm/min and 10 mm/min, and the rotary cutting results are long strips of continuous tubular tissue 2 mm (millimeter), 5 mm and 10 mm wide.

Figure 1D:
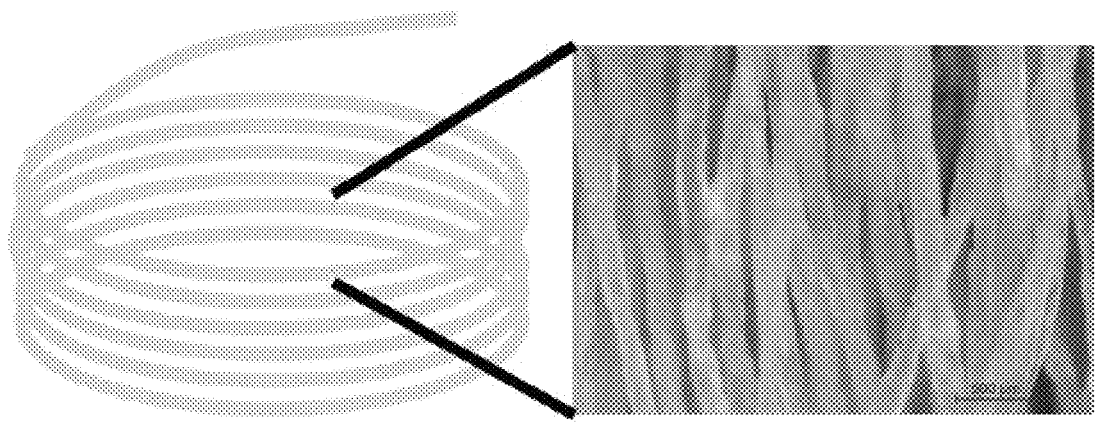
FIG. 1D is the acellular fiber of the porcine small intestinal submucosa and schematic illustration.
Figure 1E:
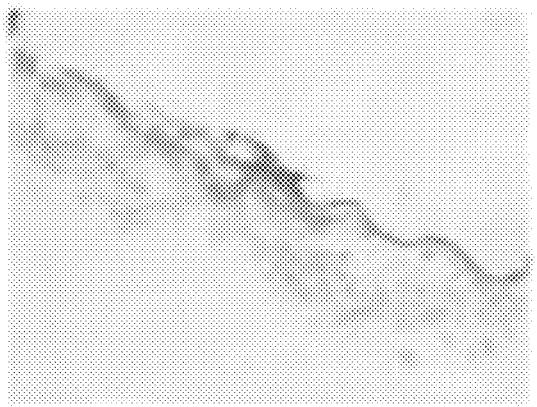
FIG. 1E is the hematoxylin eosin staining and nuclear staining diagram of porcine small intestinal submucosa after decellularization.
Figure 1E:
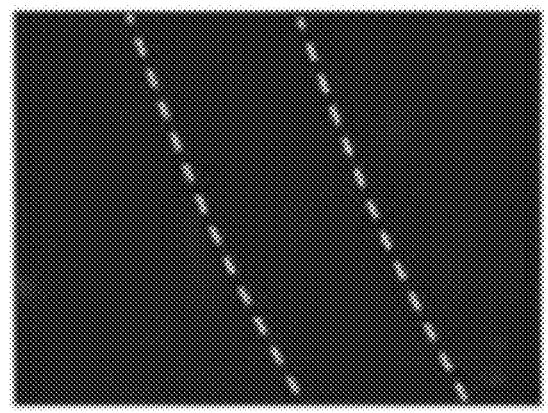
Figure 1F:
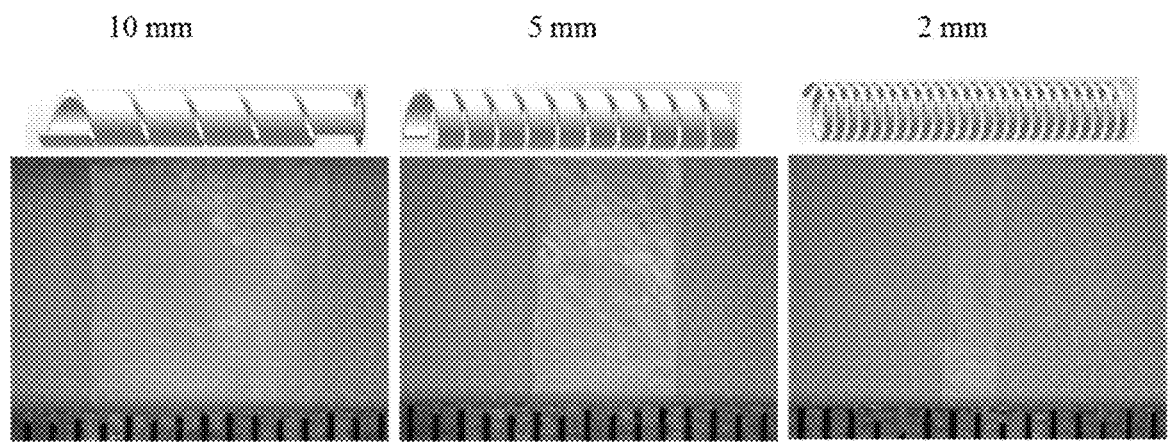
FIG. 1F is the acellular matrix strip with different widths obtained after rotary cutting.
Figure 1G:
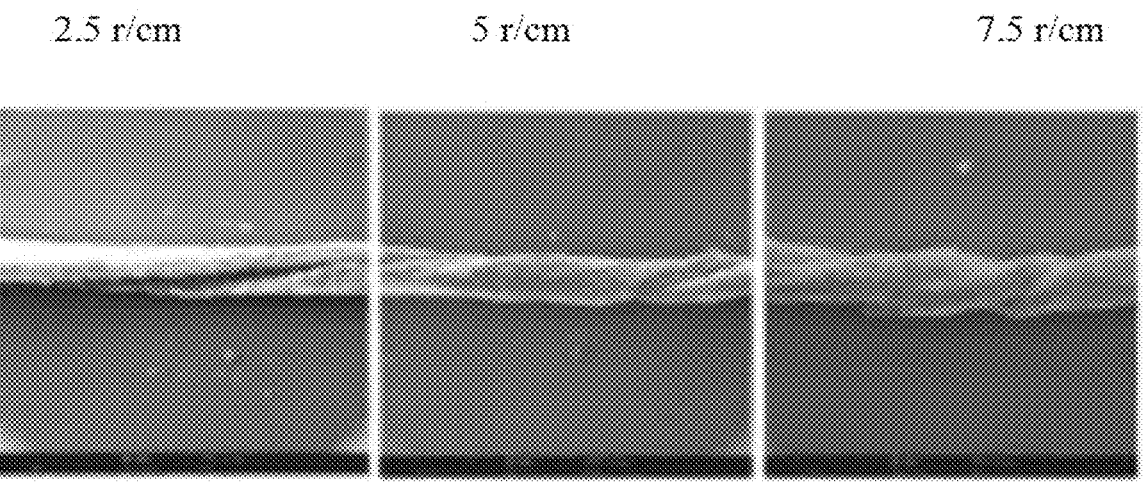
FIG. 1G is the morphology of acellular matrix fiber obtained after twisting at different rotational speeds.

S3, twisting: the acellular matrix strips are twisted into fibers by twisting and winding equipment, and automatically wound on the bobbin, with the twisting speed of 100 r/min and the winding speed of 110 r/min, and the twisting degrees of 2.5 r/cm, 5 r/cm and 7.5 r/cm (in FIG. 1D and FIG. 1G).

S4, structural design: the fiber weaving structure according to the required sponge structure is designed, and the G code for 3D printer operation is written.

S5, weft printing: 3D printing equipment is used to weave acellular matrix scaffold materials. The printing platform consists of a group of vertically inserted needles with a diameter of 21G and a length of 4 cm, with a distance of 2 mm to replace warp. Acellular matrix fibers are led out from the nozzle of the printer, wound around the needles of the printing platform according to the path controlled by the written G code, and then wound layer by layer to form the weft part of scaffold materials.

Figure 2A:
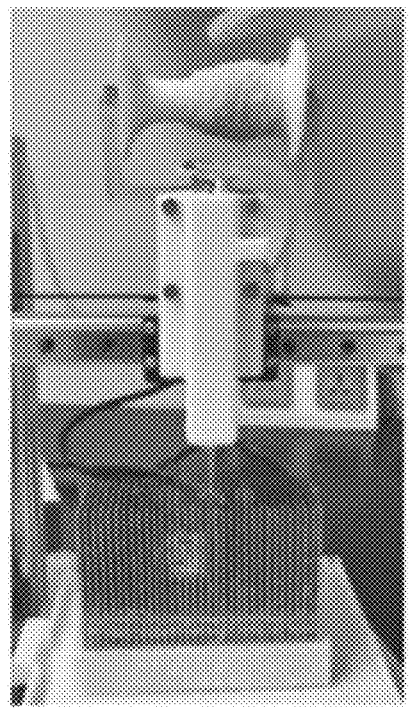
FIG. 2A is the 3D printer-aided fiber weaving diagram.
Figure 2B:
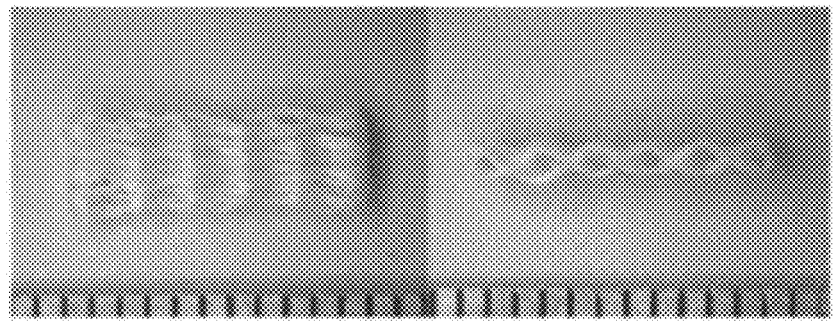
FIG. 2B is the sheet acellular matrix scaffold material of Embodiment 4.
Figure 2C:
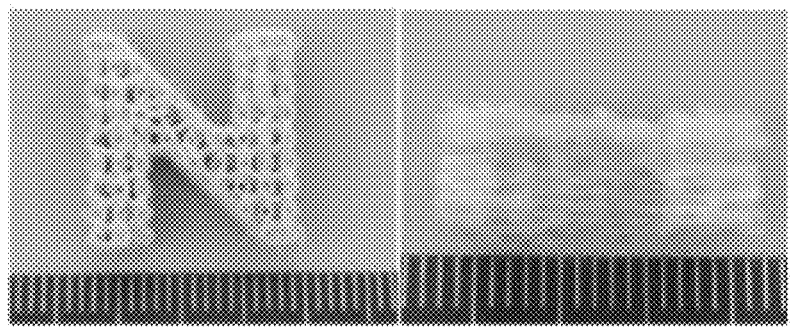
FIG. 2C is the "N" acellular matrix scaffold material of Embodiment 6.
Figure 2D:
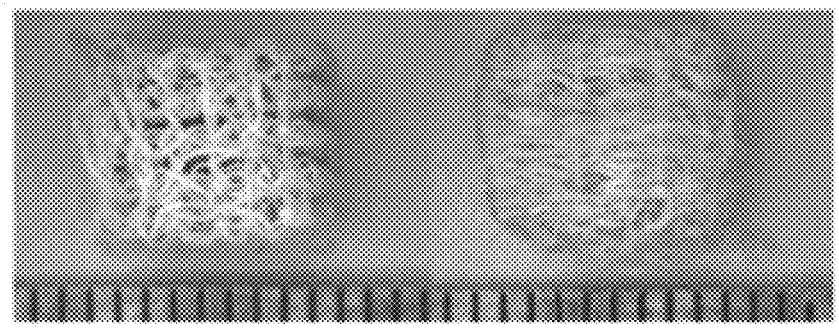
FIG. 2D is the sponge acellular matrix scaffold material obtained in Embodiment 1.

S6, warp weaving: the needle tube is pulled out from the wound scaffold material, and each row of weft is connected in series with acellular matrix fibers along the vacant part of the needle tube in an S shape to form the warp of the scaffold material. Finally, the spongy acellular matrix fiber scaffold material is obtained, as shown in FIG. 2D.

Embodiment 2

A preparation method of spongy porcine small intestinal submucosa acellular matrix fiber scaffold loaded with macrophages includes following steps:

the acellular matrix fiber scaffold material obtained in Embodiment 1 is sterilized, then soaked in the culture medium, and macrophages are inoculated on the scaffold material at a density of $5*10^4/cm^2$, cultured until the cells adhered to the wall, and then 0.5 ml of appropriate culture medium is added for a certain time.

Among them, the medium is DMEM supplemented with 10% fetal bovine serum.

Embodiment 3

The acellular small intestinal submucosa is cut into pieces of 1*0.5 cm, and then 10 layers of small intestinal submucosa are superimposed as the control group. The spongy acellular matrix fiber scaffold obtained in Embodiment 1 is implanted into the tibialis anterior muscle defect of rats as the experimental group. The specific implantation method included following steps: anesthetizing rats with isoflurane and shaving the hair at the surgical site. Scissors cut the skin and fascia layer by layer to expose the tibialis anterior muscle. A 1*0.5*0.5 cm defect is cut out with scissors, and the material is inserted into the defect area and properly suture fixation. The fascia and skin are then sutured layer by layer, and sterilized with iodophor, and the procedure is completed.

Figure 3A:
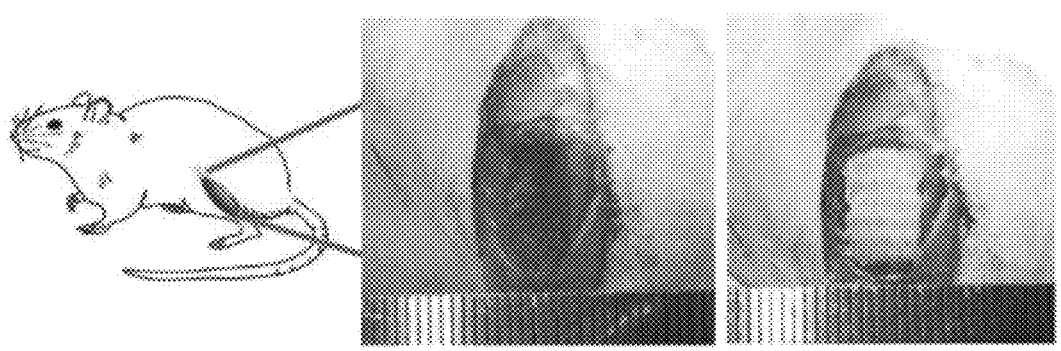
FIG. 3A is the stereogram of the tibialis anterior muscle defect and the implanted material in rats from left to right.
Figure 3B:
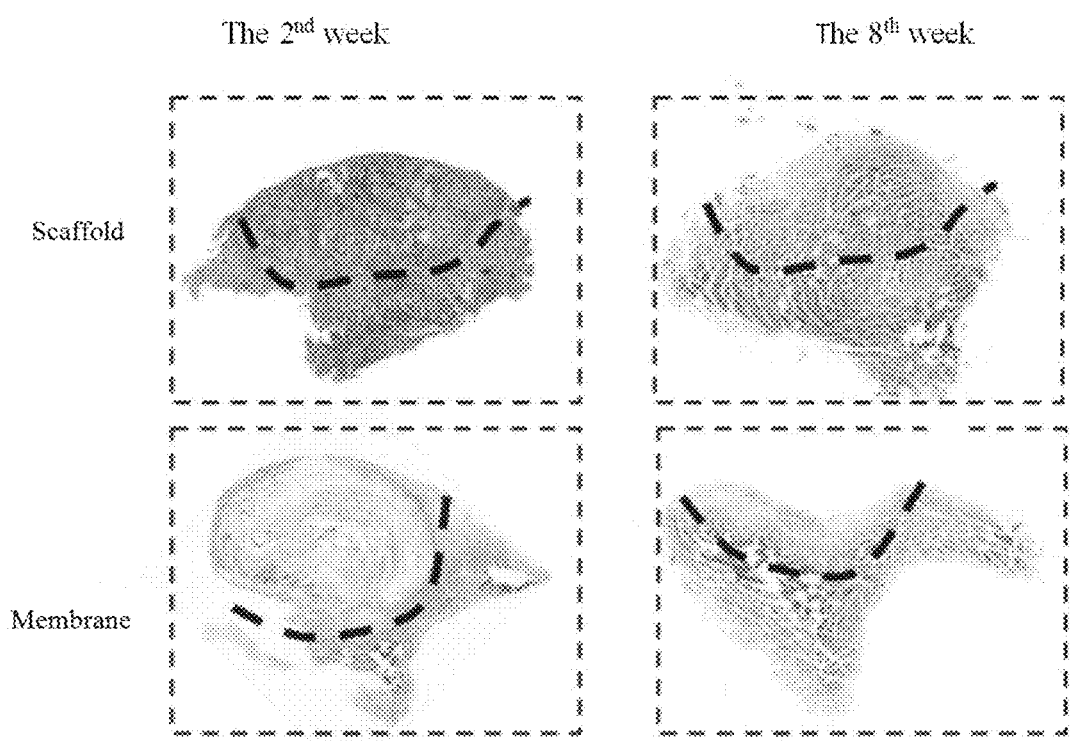
FIG. 3B is the H&E staining photos after 2 weeks and 8 weeks.

The results are shown in FIG. 3A and FIG. 3B. It is seen that in the $2^{nd}$ week, the cells in the acellular matrix fiber sponge group are fully migrated, while the cells in the control group are less infiltrated. In the $8^{th}$ week, the defects in the control group are still obvious, while the defects in the experimental group are completely filled with new muscles.

Embodiment 4

A preparation method of porcine small intestinal submucosa acellular matrix sheet fiber scaffold (in FIG. 2B) includes the following steps:

S1, decellularization: the whole or part of porcine small intestinal submucosa is put into 0.1% peracetic acid solution according to the mass ratio of tissue to solution of 1:5, and stirred for 2 h at the rate of 60 r/min for disinfection. Take it out, wash it with water for three times, put it into 1% sodium dodecyl sulfate solution according to the mass ratio of tissue to solution of 1:5, stir and wash at 50 r/min, change the solution every 8 hours and wash for 1 day. Then, according to the mass ratio of tissue to water of 1:5, water is stirred and washed at the stirring speed of 80 r/min, and the solution is changed every 3h, and washed for 3 days respectively. Tissue and solution are washed with Tris-HCL solution (50 units/mL DNA enzymes+1 unit/mL RNA enzymes) containing DNA and RNA enzymes according to the mass ratio of 1:5 at 70 r/min and 37° C. enzyme washing for 10 h, then taken out and washed with water for 3 days to obtain acellular tubular tissue.

S2, rotary cutting: the acellular tubular tissue is sleeved on a metal rod, and then the metal rod is fixed on a rotary cutting device, and the surface of the rod is rotary cut by using a cutter in a spiral trajectory, and the rotation speed of the metal rod is set at 50 r/min, and the transverse speed of the cutter is 30 mm/min, and the rotary cutting results are continuous long strips 2 mm in width.

S3, twisting: the acellular matrix strips are twisted into fibers by twisting and winding equipment, and automatically wound on the bobbin, with the twisting speed of 100 r/min and the winding speed of 110 r/min, and the twisting degrees of 2.5 r/cm.

S4, structural design: the fiber weaving structure according to the required sponge structure is designed, and the G code for 3D printer operation is written.

S5, weft printing: 3D printing equipment is used to weave acellular matrix scaffold materials. The printing platform consists of a group of vertically inserted needles with a diameter of 21G and a length of 4 cm, with a distance of 2 mm to replace warp. Acellular matrix fibers are led out from the nozzle of the printer, wound around the needles of the printing platform according to the path controlled by the written G code, and then wound layer by layer to form the weft part of scaffold materials.

S6, warp weaving: the needle tube is pulled out from the wound scaffold material, and each row of weft is connected in series with acellular matrix fibers along the vacant part of the needle tube in an S shape to form the warp of the scaffold material. Finally, the sheet acellular matrix fiber scaffold material is obtained.

Embodiment 5

A preparation method of porcine small intestinal submucosa acellular matrix sheet fiber scaffold loaded with L6 cells includes following steps:

the massive acellular matrix fiber scaffold material obtained in Embodiment 4 is sterilized and then soaked in the culture medium. L6 cells are inoculated on the scaffold material at a density of $1*105/cm^2$, cultured until the cells adhered to the wall, and then 1 mL of culture medium is added until the cell confluence is 85% before transplantation.

Among them, the medium is a low-sugar basic medium supplemented with 10% fetal bovine serum.

Figure 4A:
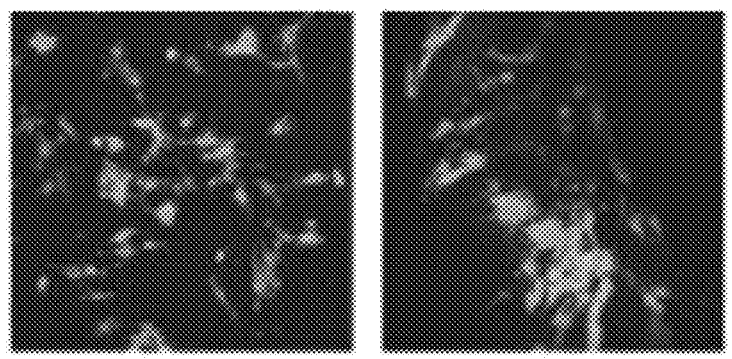
FIG. 4A is the L6 cells planted on acellular matrix fiber woven materials and membrane-like scaffold materials.
Figure 4A:
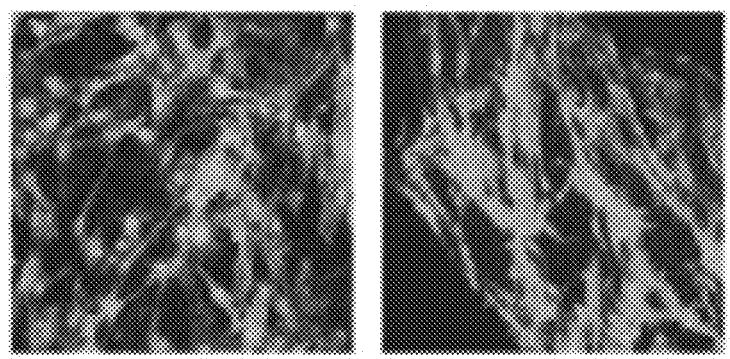
Figure 4A:
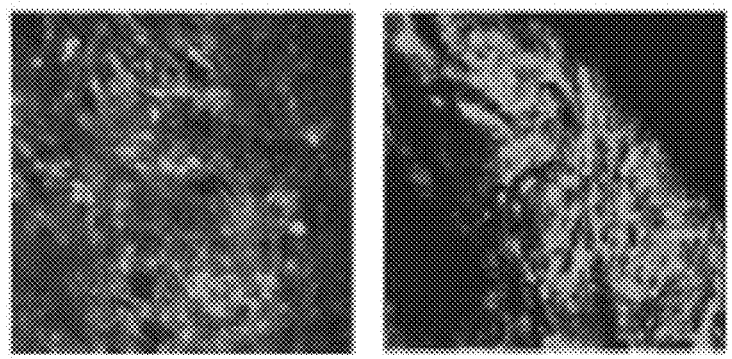
Figure 4B:
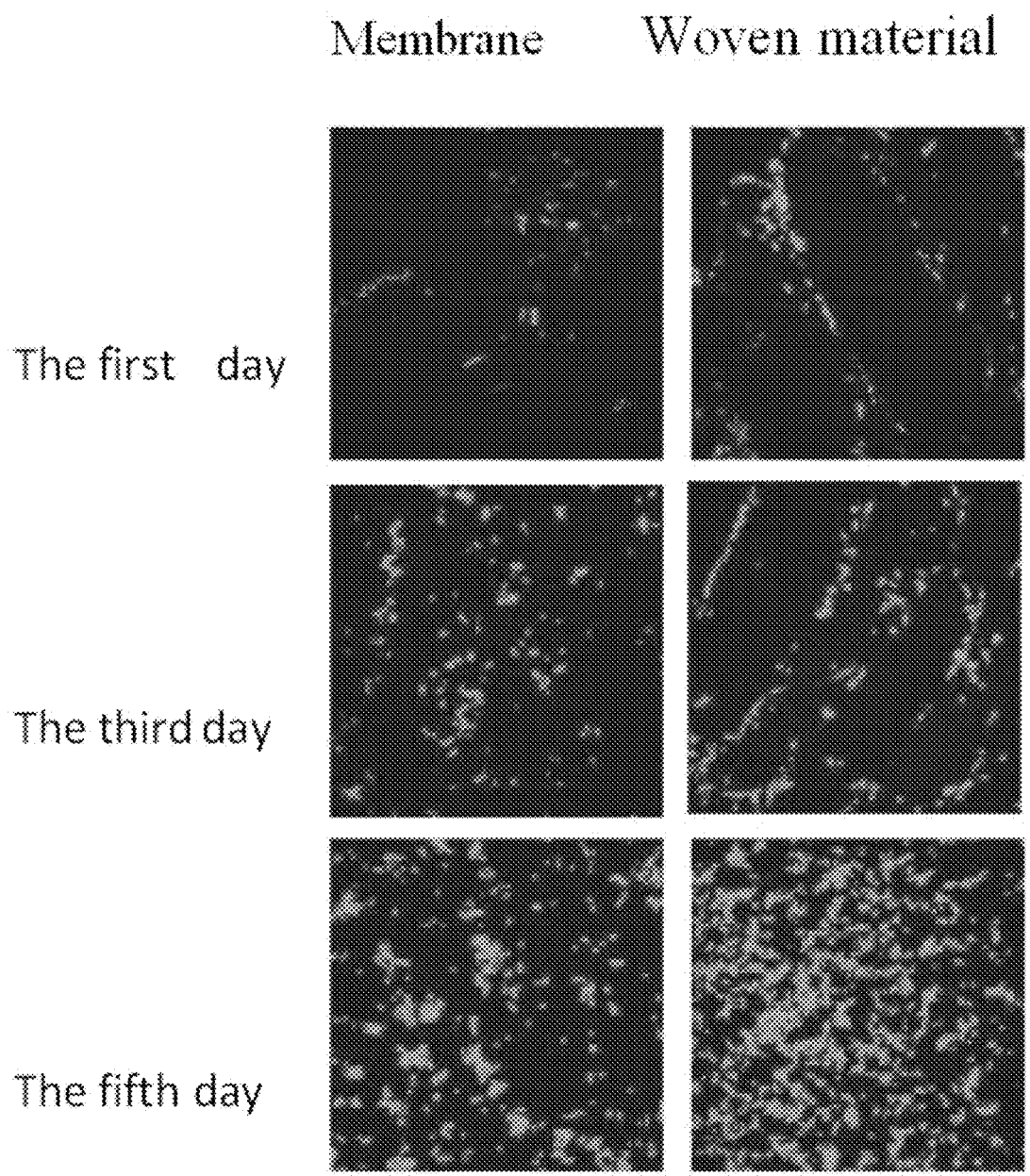
FIG. 4B is the result of live and dead staining.

FIG. 4A and FIG. 4B show cells loaded with acellular matrix fiber scaffold in Embodiment 5; FIG. 4A indicates that L6 cells are planted on acellular matrix fiber woven materials and membrane-like scaffold materials. It can be seen that the cells spread well at 1, 3 and 5 days, and FIG. 4B indicates that the cells survive well after being cultured on acellular matrix fiber woven materials and membrane-like scaffold materials for 1, 3 and 5 days.

Embodiment 6

A preparation method of an N-shaped bovine small intestinal submucosa acellular matrix fiber scaffold (in FIG. 2C) includes the following steps:

S1, decellularization: the whole or part of bovine small intestinal submucosa is put into 0.1% peracetic acid solution according to the mass ratio of tissue to solution of 1:5, and stirred for 2 h at the rate of 50 r/min for disinfection. After disinfection, take it out, wash it with water for three times, put it into 1% sodium dodecyl sulfate solution according to the mass ratio of tissue to solution of 1:5, stir and wash at 50 r/min, change the solution every 6 hours and wash for 1 day. Then, according to the mass ratio of tissue to water of 1:5, water is stirred and washed at the stirring speed of 60 r/min, and the solution is changed every 4h, and washed for 3 days respectively. Tissue and solution are washed with Tris-HCL solution (50 units/mL DNA enzymes+1 unit/mL RNA enzymes) containing DNA and RNA enzymes according to the mass ratio of 1:5 at 70 r/min and 37° C. enzyme washing for 8 h, then taken out and washed with water for 3 days to obtain acellular tubular tissue.

S2, rotary cutting: the acellular tubular tissue is sleeved on a metal rod, and then the metal rod is fixed on a rotary cutting device, and the surface of the rod is rotary cut by using a cutter in a spiral trajectory, and the rotation speed of the metal rod is set at 60 r/min, and the transverse speed of the cutter is 40 mm/min, and the rotary cutting results are continuous long strips 3 mm in width.

S3, twisting: the acellular matrix strips are twisted into fibers by twisting and winding equipment, and automatically wound on the bobbin, with the twisting speed of 100 r/min and the winding speed of 130 r/min, and the twisting degrees of 3 r/cm.

S4, structural design: the fiber weaving structure according to the required N-shaped structure is designed, and the G code for 3D printer operation is written.

S5, weft printing: 3D printing equipment is used to weave acellular matrix scaffold materials. The printing platform consists of a group of vertically inserted needles with a diameter of 21G and a length of 3 cm, with a distance of 2 mm to replace warp. Acellular matrix fibers are led out from the nozzle of the printer, wound around the needles of the printing platform according to the path controlled by the written G code, and then wound layer by layer to form the weft part of scaffold materials.

S6, warp weaving: the needle tube is pulled out from the wound scaffold material, and each row of weft is connected in series with acellular matrix fibers along the vacant part of the needle tube in an S shape to form the warp of the scaffold material. Finally, the N-shaped acellular matrix fiber scaffold material is obtained.

Embodiment 7

A preparation method of spongy sheep small intestinal submucosa acellular matrix fiber scaffold includes following steps:

S1, decellularization: the whole or part of sheep small intestinal submucosa is put into 0.1% peracetic acid solution according to the mass ratio of tissue to solution of 1:5, and stirred for 2 h at the rate of 70 r/min for disinfection. After disinfection, take it out, wash it with water for three times, put it into 1% sodium dodecyl sulfate solution according to the mass ratio of tissue to solution of 1:5, stir and wash at 70 r/min, change the solution every 9 hours and wash for 1 day.

Then, according to the mass ratio of tissue to water of 1:5, water is stirred and washed at the stirring speed of 70 r/min, and the solution is changed every 4h, and washed for 3 days respectively. Tissue and solution are washed with Tris-HCL solution (50 units/mL DNA enzymes+1 unit/mL RNA enzymes) containing DNA and RNA enzymes according to the mass ratio of 1:5 at 70 r/min and 37° C. enzyme washing for 12 h, then taken out and washed with water for 3 days to obtain acellular tubular tissue.

S2, rotary cutting: the acellular tubular tissue is sleeved on a metal rod, and then the metal rod is fixed on a rotary cutting device, and the surface of the rod is rotary cut by using a cutter in a spiral trajectory, and the rotation speed of the metal rod is set at 70 r/min, and the transverse speed of the cutter is 50 mm/min, and the rotary cutting results are continuous long strips 4 mm in width.

S3, twisting: the acellular matrix strips are twisted into fibers by twisting and winding equipment, and automatically wound on the bobbin, with the twisting speed of 90 r/min and the winding speed of 100 r/min, and the twisting degrees of 2.5 r/cm.

S4, structural design: the fiber weaving structure according to the required spongy structure is designed, and the G code for 3D printer operation is written.

S5, weft printing: 3D printing equipment is used to weave acellular matrix scaffold materials. The printing platform consists of a group of vertically inserted needles with a diameter of 21G and a length of 5 cm, with a distance of 2 mm to replace warp. Acellular matrix fibers are led out from the nozzle of the printer, wound around the needles of the printing platform according to the path controlled by the written G code, and then wound layer by layer to form the weft part of scaffold materials.

S6, warp weaving: the needle tube is pulled out from the wound scaffold material, and each row of weft is connected in series with acellular matrix fibers along the vacant part of the needle tube in an S shape to form the warp of the scaffold material. Finally, the spongy acellular matrix fiber scaffold material is obtained.

Embodiment 8

A preparation method of tubular bovine carotid artery acellular matrix tubular stent (in FIG. 2E) includes the following steps:

S1, decellularization: the whole or part of tubular bovine carotid artery is put into 0.1% peracetic acid solution according to the mass ratio of tissue to solution of 1:5, and stirred for 2 h at the rate of 50 r/min for disinfection. After disinfection, take it out, wash it with water for three times, put it into 1% sodium dodecyl sulfate solution according to the mass ratio of tissue to solution of 1:5, stir and wash at 50 r/min, change the solution every 5 hours and wash for 3 days. Then, according to the mass ratio of tissue to water of 1:5, water is stirred and washed at the stirring speed of 70 r/min, and the solution is changed every 4h, and washed for 3 days respectively. Tissue and solution are washed with Tris-HCL solution (50 units/mL DNA enzymes+1 unit/mL RNA enzymes) containing DNA and RNA enzymes according to the mass ratio of 1:5 at 50 r/min and 37° C. enzyme washing for 20 h, then taken out and washed with water for 3 days to obtain acellular tubular tissue.

S2, rotary cutting: the acellular tubular tissue is sleeved on a metal rod, and then the metal rod is fixed on a rotary cutting device, and the surface of the rod is rotary cut by using a cutter in a spiral trajectory, and the rotation speed of the metal rod is set at 80 r/min, and the transverse speed of the cutter is 50 mm/min, and the rotary cutting results are continuous long strips 3.5 mm width.

S3, twisting: the acellular matrix strips are twisted into fibers by twisting and winding equipment, and automatically wound on the bobbin, with the twisting speed of 90 r/min and the winding speed of 110 r/min, and the twisting degrees of 3 r/cm.

S4, structural design: the fiber weaving structure according to the required tubular structure is designed, and the G code for 3D printer operation is written.

S5, weft printing: 3D printing equipment is used to weave acellular matrix scaffold materials. The printing platform consists of a group of vertically inserted needles with a diameter of 21G and a length of 10 cm, with a distance of 1.5 mm to replace warp. Acellular matrix fibers are led out from the nozzle of the printer, wound around the needles of the printing platform according to the path controlled by the written G code, and then wound layer by layer to form the weft part of scaffold materials.

Figure 2E:
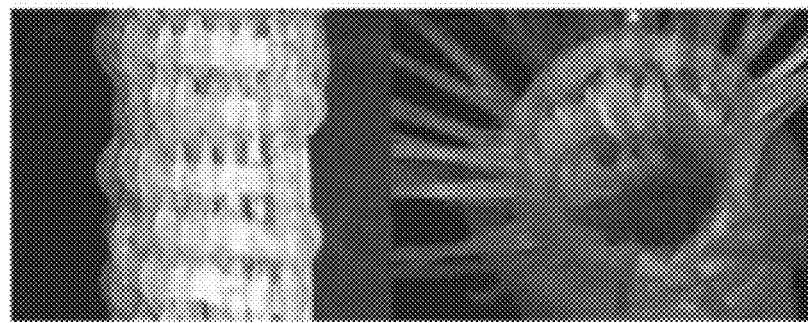
FIG. 2E is the tubular bovine carotid artery acellular matrix scaffold material obtained in Embodiment 8.

S6, warp weaving: the needle tube is pulled out from the wound scaffold material, and each row of weft is connected in series with acellular matrix fibers along the vacant part of the needle tube in an S shape to form the warp of the scaffold material. Finally, the tubular acellular matrix fiber scaffold material is obtained (as shown in FIG. 2E).

Embodiment 9

A preparation method of bovine carotid artery acellular matrix tubular stent loaded with human umbilical vein endothelial cells includes following steps:

cell loading: the tubular acellular matrix fiber scaffold material obtained in Embodiment 7 is sterilized and then soaked in the culture medium. The human umbilical vein endothelial cells are seeded on the scaffold material at a density of $8*10^4/cm^2$, cultured until the cells adhered to the wall, and then 2 ml of culture medium is added for a certain time before transplantation.

Among them, the medium is DMEM supplemented with 10% fetal bovine serum and 1% penicillin streptomycin.

The above are only preferred embodiments of this disclosure, but the protection scope of this disclosure is not limited to this. Any change or replacement that may be easily thought of by a person skilled in the art within the technical scope disclosed in this application should be covered by this disclosure. Therefore, the protection scope of this disclosure should be defined by the protection scope of the claims.

What is claimed is:

1. A preparation method of acellular matrix woven material, wherein the acellular matrix woven material is prepared by 3D printing in conjunction with a weaving method; specifically comprising the following steps:

cutting acellular animal tubular tissue with a rotary cutting method, twisting, and weaving warps after the 3D printing wefts to obtain the acellular matrix woven material, wherein the rotary cutting method comprises the following steps:

sleeving the acellular animal tubular tissue on a cylindrical mold, fixing on a rotary cutting device, and then cutting with a knife or laser in a spiral trajectory to obtain continuous acellular matrix strips; and the weaving the warps after the 3D printing the wefts specifically comprises the following steps:

designing a weaving structure of a scaffold material according to a required macro shape, writing corresponding G code, printing acellular matrix fibers on a platform with regularly arranged needle tubes, weaving wefts of the scaffold material, replacing the needle tubes with the acellular matrix fibers, and weaving the warps of the scaffold material.

2. The preparation method according to claim 1, wherein the animal tubular tissue is one among small intestine, large intestine, artery and vein; and the animals comprise one or more among pigs, cattle, sheep, dogs, horses, rats and rabbits.

3. A acellular matrix woven material prepared by the preparation method according to claim 1.

4. The acellular matrix woven material according to claim 3, wherein a micro-woven structure of the acellular matrix woven material is one among plain weave, twill weave and satin weave fixed by interweaving and interlocking warps and wefts.

* * * * *